United States Patent [19]

Pollock

[11] Patent Number: 5,054,194
[45] Date of Patent: Oct. 8, 1991

[54] METHOD FOR CONTROLLING BONDING WIRE LOOP WEIGHT

[75] Inventor: Randy Pollock, Scottsdale, Ariz.

[73] Assignee: Motorola, Inc., Schaumburg, Ill.

[21] Appl. No.: 649,261

[22] Filed: Jan. 30, 1991

Related U.S. Application Data

[63] Continuation of Ser. No. 430,543, Nov. 2, 1989, abandoned.

[30] Foreign Application Priority Data

Feb. 13, 1989 [JP] Japan .................................. 1-311145

[51] Int. Cl.$^5$ ........................ H05K 3/34; B23K 31/02
[52] U.S. Cl. ...................................... 29/840; 29/593; 29/850; 228/4.5; 228/179
[58] Field of Search ................. 29/840, 842, 846, 850, 29/593; 228/4.5, 179; 219/56.21

[56] References Cited

U.S. PATENT DOCUMENTS

| | | | |
|---|---|---|---|
| 4,226,710 | 5/1981 | Bilane et al. | 228/4.5 |
| 4,327,860 | 5/1982 | Kirshenboin et al. | 228/179 |
| 4,925,085 | 5/1990 | Buxton | 228/179 |

FOREIGN PATENT DOCUMENTS 2146937  5/1985  United Kingdom ................ 228/179

Primary Examiner—Joseph M. Gorskl
Assistant Examiner—Peter Dungba Vo
Attorney, Agent, or Firm—Dale E. Jepsen; Eugene A. Parsons

[57] ABSTRACT

A method for controlling the wire loop height of wires installed during the manufacture of an electronic module with a wire bond machine provides for making adjustments based on the wire loop height adjustment resolution of the wire bond machine itself, rather than on an electrical performance specification tolerance for the module.

3 Claims, 2 Drawing Sheets

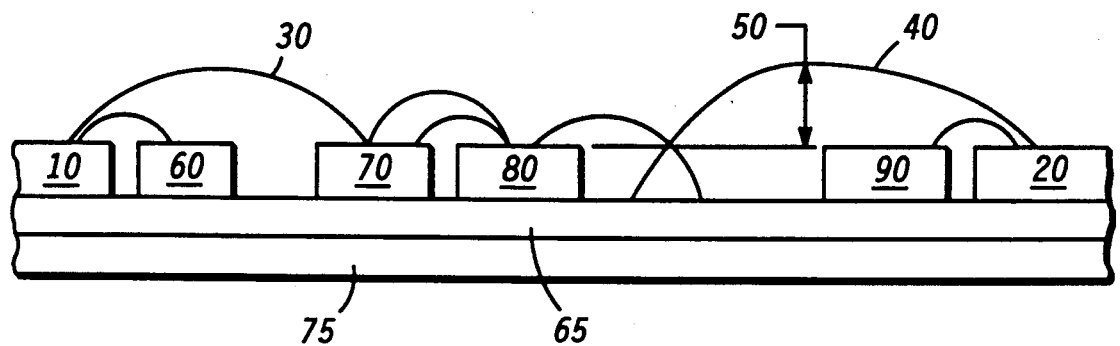
FIG. 1
FIG. 2
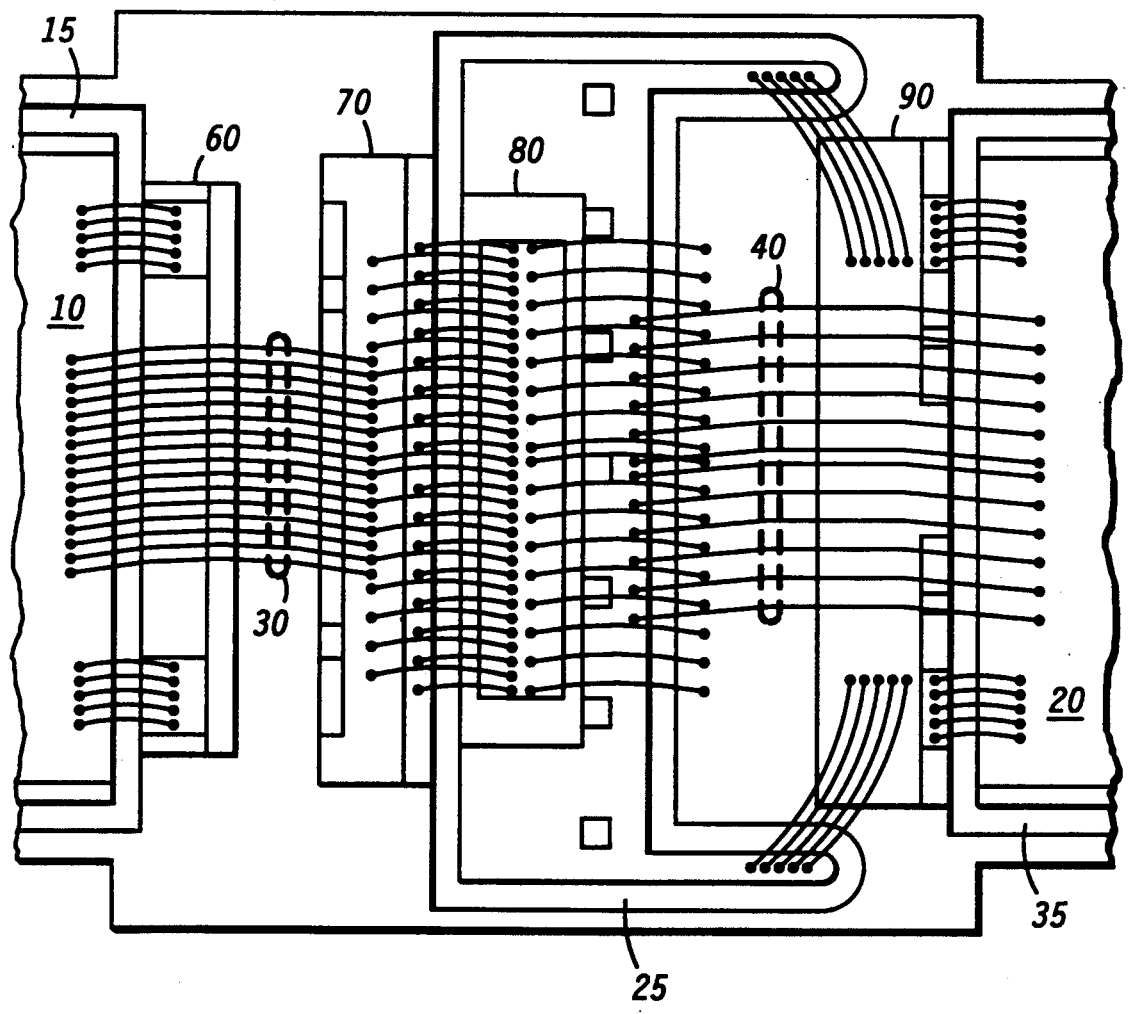

METHOD FOR CONTROLLING BONDING WIRE LOOP WEIGHT

This application is a continuation of prior application Ser. No. 07/430,543, filed Nov. 2, 1989, now abandoned.

BACKGROUND OF THE INVENTION

This invention relates in general to the manufacture of electronic modules and more particularly to a method for controlling the loop height for wires used to interconnect specific circuit elements contained in such modules.

During the manufacture of certain electronic modules an apparatus called a wire bonder is used to provide an electrical connection between circuit elements using a plurality of wires. In certain RF modules the plurality of wires is used to provide a specific amount of inductance, and the height of such wires above a given reference plane within the module must therefore be controlled to a relatively close tolerance. Ordinarily this tolerance is selected based on the variation in one or more electrical performance specifications which occurs as a result of the variation in the height of these wires above the reference plane.

During manufacture the actual height of the connecting wires is ordinarily allowed to vary within this tolerance based on the electrical specification, and adjustments to the wire bond apparatus are made only when the wire height is outside tolerance based on the electrical specifications for the module.

Depending on the sampling rate used and the particular wire bond apparatus being used, the wire loop height may in a given case not only vary significantly from a desired nominal wire loop height, but in fact exceed the tolerance based on electrical specifications for a certain number of individual modules prior to detection by measurement of a given sample.

SUMMARY OF THE INVENTION

It is therefore an object of the present invention to provide a method for controlling the wire loop height of a electronic module wherein the amount by which a given wire loop height is allowed to vary from a desired nominal height is based not on a given electrical specification, but on the adjustment resolution of a given wire bond apparatus.

It is further an object of the present invention to provide a method for controlling wire loop height wherein specific wire loop height measurements are evaluated using a programmed digital computer which then calculates a difference between the average actual wire loop height and a desired nominal height and provides an operator with a desired magnitude and direction for an adjustment to a given wire bond apparatus.

The foregoing and other objects are achieved in the present invention wherein there is provided a method for controlling wire loop height which comprises the steps of mounting one or more circuit elements on a mounting surface, connecting one or more designated areas of a given circuit element to other circuit elements or to designated areas of the mounting surface using a wire bonder to attach a plurality of wires therebetween, measuring the actual wire loop height for a given plurality of wires, calculating the average actual wire loop height, and adjusting the commanded wire loop height of the wire bonder when the average actual wire loop height differs from a desired nominal value by approximately the adjustment resolution of the wire bonder. In a preferred embodiment the steps of calculating the average actual wire loop height and comparing this average to the desired nominal value are accomplished using a computer program.

BRIEF DESCRIPTION OF THE DRAWINGS

The above and other features and objects of the present invention and the manner of attaining them will become more apparent and the invention itself will be best understood by reference to the following description of an embodiment of the invention taken in conjunction with the accompanying drawings wherein:

FIG. 1 is a side view of a typical RF electronic module illustrating the critical wire loop height associated therewith;

FIG. 2 is a top view of this module showing the layout of specific circuit elements and interconnecting wires.

DESCRIPTION OF A PREFERRED EMBODIMENT

Figure 3:
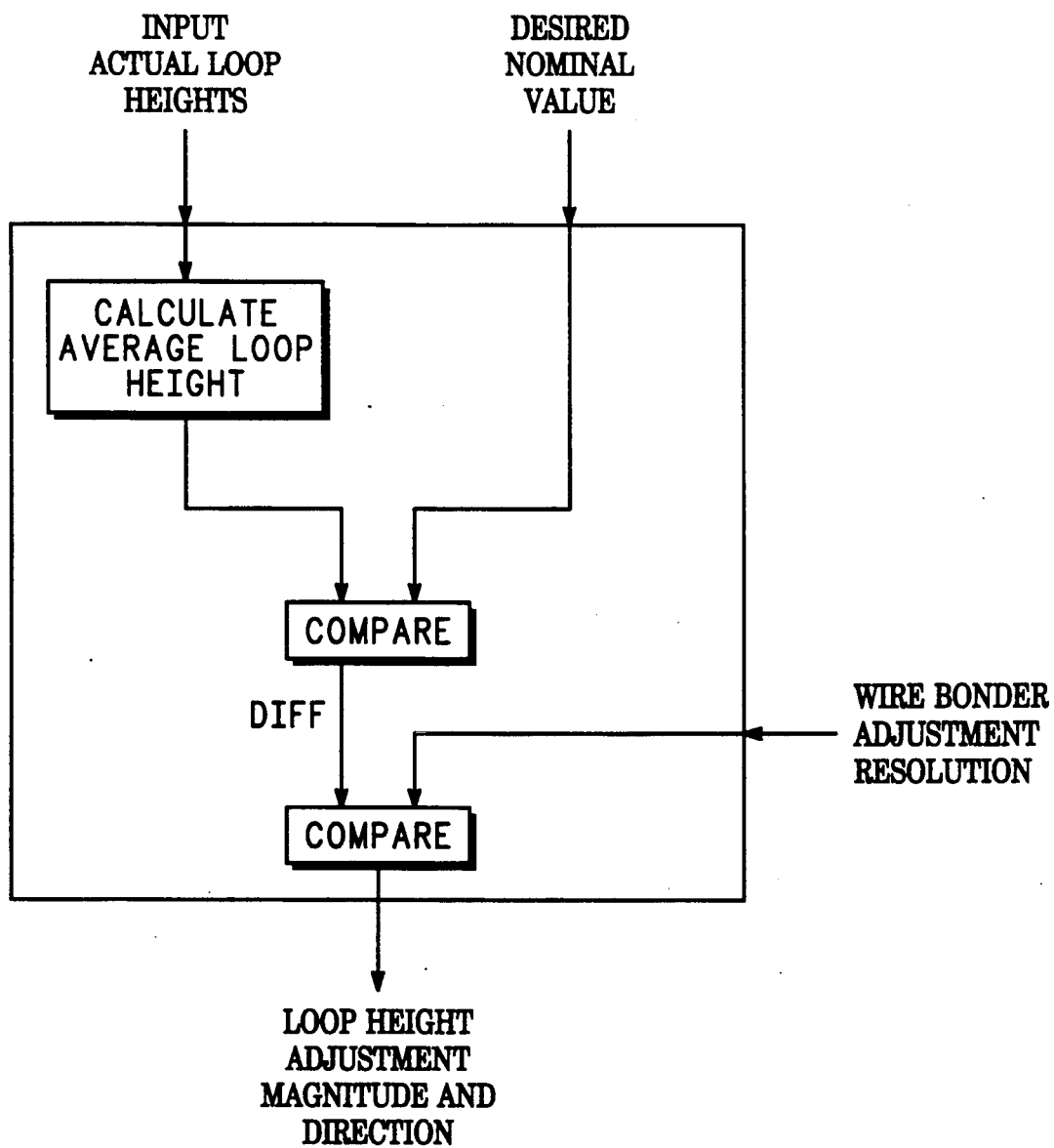
FIG. 3 shows a flowchart illustrating the wire loop height adjustment method of the present invention.

FIGS. 1 and 2 are respective side and top views of a typical RF module which might be constructed using a wire loop height adjustment method in accordance with the present invention. Such a module may be constructed, for example, by applying a metalized layer 65 over an insulating substrate 75 and then attaching individual circuit elements to predetermined portions of the metalized layer.

Voids 15, 25, and 35, as shown in FIG. 2, are used to isolate certain portions of the metalized layer from each other. Specific circuit elements such as capacitors 60, 70, and 90 and a transistor die 80 are placed on the metalized layer in predetermined locations. Areas 10 and 20 would be, for example, respective input and output terminals for external connection of the module.

As can be seen, groups of wires are then used to interconnect the various circuit elements and portions of the metalized layer. For example, wire group 30 is used to connect input terminal 10 to capacitor 70. In a similar fashion wire group 40 is used to connect output terminal 20 to that portion of the metalized layer within isolation region 25.

It is the height of these and other wire loops, illustrated for example as dimension 50 for wire group 40 in FIG. 1, which determines the inductance of the connection between the circuit elements in question. Depending on the specific electrical circuit and the operating frequency, this inductance value, and therefore the height of a given wire loop above a reference plane such as the top of transistor die 80, may be very critical and therefore must be controlled to a specific tolerance.

Ordinarily the allowable tolerance for these wire loop heights would be based upon the variation of one or more electrical characteristics of the circuit with variations in the wire loop height. While this may be satisfactory from a performance standpoint, the allowable tolerance based on the electrical characteristics may in some cases allow a significant variation of the wire loop height from a desired nominal value. Depending on the particular wire bond machine being used and other factors, certain individual modules may in fact exceed the desired tolerance before the out-of-tolerance condition is discovered by measuring the wire loop height of a specific periodic sample module.

In some cases the particular wire bond apparatus being used may have a wire height adjustment resolution which would allow for corrections to the wire height in much smaller increments than would be necessary to maintain the wire height within the tolerances required by the electrical specifications. In these cases it has been found desirable to utilized a tolerance, and make wire height adjustments to the wire bond apparatus, based not on the requirements for any given electrical specifications, but on the adjustment resolution of the wire bond apparatus itself.

By making these adjustments based on the wire bond apparatus adjustment resolution the actual average wire bond height is maintained at a value much closer to the desired nominal value thus greatly reducing the likelihood that any modules will be manufactured which exceed the larger tolerance based on the electrical specifications of the circuit in question.

In a preferred embodiment the actual measurements of the wire heights for a given group of wires, such as group 40, are evaluated using a programmed digital computer which calculates the average of these actual measurements, compares this average actual value with the desired nominal value, compares this difference to the adjustment resolution of the wire bond apparatus and provides as an output a desired wire bond apparatus loop height adjustment magnitude and direction. The wire bond machine operator may therefore simply enter sample measurements into the computer and immediately obtain the desired adjustment, if any, to be applied to a given wire loop height. These steps are illustrated in the flowchart of FIG. 3.

EXAMPLE

In the module shown in FIGS. 1 and 2, metalized layer 65 is applied to a beryllium oxide insulating layer 75, and MOS capacitors 60, 70, and 90, as well as transistor die 80, are applied to appropriate areas of the metalized layer. Wires are then attached utilizing a wire bond machine such as, for example, a K&S 1470 manufactured by Kulicke and Soffa Industries of Harshima, Pa. For some of the typical wire bond heights in question the allowable tolerance based on electrical parameters may be on the order of 0.0375 to 0.0500 millimeter (1½ to 2 mils), while the adjustment resolution of the wire bond machine itself is on the order of 0.0125 millimeter (½ mil). Depending on the difference between the average actual measurement of the wire loop height of a given group of wires and the desired nominal value, the commanded wire loop height is adjusted up or down a number of motor counts wherein one motor count is the smallest amount of wire height adjustment available for the wire bond machine.

This method provides much closer control over the wire loop height of the wires used to interconnect specific circuit elements of a given electronic module and therefore reduces the probability of producing modules having interconnecting wires which exceed the wire loop height tolerances based on the electrical specifications of the module.

What has been provided therefore is a method for controlling wire loop height in connection with a wire bond apparatus wherein changes to the desired or commanded wire loop height are made based on the available adjustment resolution of the wire bond apparatus itself rather than a larger tolerance based on the desired electrical performance of the module in question.

While the above description is given in connection with a specific wire bond machine and electronic module it is to be understood that the inventive method may be used in any application where the adjustment capability of the wire bond machine is greater than the tolerance which would otherwise be required for the wire loop height based on electrical specifications of the module in question. Changes in form and detail may be made by one skilled in the art without departing from the scope of the invention as described in the appended claims.

I claim:

1. A method for controlling wire loop height during the manufacture of electronic assemblies, comprising the steps of:

mounting at least one circuit element on a mounting surface of each of the assemblies and establishing a reference plane relative to the at least one circuit element on each of the assemblies, each of the assemblies being adapted to have bonded thereto pluralities of wires requiring an intended loop height above the reference plane plus or minus a certain amount in order for the electronic assembly to meet predetermined electrical specifications;

bonding a plurality of wires between the at least one circuit element and another circuit element or a predetermined area of the mounting surface of a first one of the assemblies using a wire bonder having a commanded wire loop height corresponding nominally to the intended wire loop height, thereby producing a plurality of bonded wires each having an actual loop height above the reference plane of the first one of the assemblies, the wire bonder having an adjustment for changing the commanded wire loop height by a predetermined amount to alter the actual wire loop height of subsequently bonded wires;

measuring the actual loop height of each of the plurality of bonded wires on the first one of the assemblies;

calculating an average actual loop height from the measured actual loop heights for the plurality of bonded wires on the first one of the assemblies;

comparing the calculated average actual loop height to the intended loop height to determine a difference; and adjusting the commanded wire loop height of the wire bonder when the calculated average actual loop height differs from the intended loop height by at least the predetermined amount, thereby reducing the difference between the intended loop height and the actual loop height of bonded wires in a second and subsequent electronic assemblies.

2. The method for controlling wire loop height in accordance with claim 1 wherein said calculating and comparing steps are accomplished in a programmed digital computer and wherein the wire bonder has a minimum height adjustment for changing the commanded wire loop height and the adjusting step comprises adjusting the commanded wire loop height by one or more multiples of the minimum height adjustment whenever the difference exceeds the minimum height adjustment.

3. A method for controlling wire loop height during the manufacture of a plurality of electronic modules comprising the steps of:

mounting at least one circuit element on a mounting surface of each of the plurality of electronic modules and establishing a reference plane relative to the at least one circuit element on each of the plurality of electronic modules, each of the plurality of electronic modules being adapted to have attached thereto pluralities of wires requiring an intended loop height above the reference plane plus or minus a certain amount in order for the electronic module to meet predetermined electrical specifications;

connecting the at least one circuit element on a first one of the plurality of electronic modules to another such circuit element or to a predetermined area of the mounting surface on the first one of the plurality of electronic modules using a wire bonder to attach a plurality of wires therebetween, each of the plurality of attached wires having an actual loop height above the reference plane on the first one of the plurality of electronic modules, the wire bonder having an adjustment for changing a commanded wire loop height by a predetermined minimum amount to alter the actual loop height of subsequently attached wires;

measuring the actual loop height of each of the plurality of attached wires on the first one of the plurality of electronic modules;

calculating an average actual loop height for the plurality of attached wires on the first one of the plurality of electronic modules from the measured actual loop heights;

comparing the calculated average actual loop height to the intended loop height to obtain a difference;

comparing the difference to the predetermined minimum amount of the wire bonder adjustment; and adjusting the commanded wire loop height of the wire bonder by the predetermined minimum amount or a multiple thereof when the difference exceeds the predetermined minimum amount, thereby reducing the difference.

* * * * *